(12) United States Patent
Takizawa et al.

(10) Patent No.: US 8,825,147 B2
(45) Date of Patent: Sep. 2, 2014

(54) CARDIAC MUSCLE EXCITATION WAVEFORM DETECTOR

(71) Applicant: Nihon Kohden Corporation, Tokyo (JP)

(72) Inventors: Koji Takizawa, Tokyo (JP); Tatsuo Nishihara, Tokyo (JP); Yuuho Iwanaga, Tokyo (JP); Satoshi Suzuki, Tokyo (JP); Naoki Hattori, Tokyo (JP); Hiroki Yuze, Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 0 days.

(21) Appl. No.: 13/785,800

(22) Filed: Mar. 5, 2013

(65) Prior Publication Data

US 2013/0245476 A1     Sep. 19, 2013

(30) Foreign Application Priority Data

Mar. 15, 2012   (JP) ................................. 2012-058748

(51) Int. Cl.
*A61B 5/04* (2006.01)
*A61B 5/02* (2006.01)
*A61B 5/046* (2006.01)
*A61B 5/00* (2006.01)

(52) U.S. Cl.
CPC ............... *A61B 5/046* (2013.01); *A61B 5/7235* (2013.01)
USPC ............................. 600/518; 600/508; 600/509

(58) Field of Classification Search
USPC .......................................... 600/508–509, 518
See application file for complete search history.

(56) References Cited

U.S. PATENT DOCUMENTS

| 7,437,190 B1 | 10/2008 | Hoberman et al. |
| 2006/0095085 A1* | 5/2006 | Marcus et al. .................. 607/17 |
| 2007/0208260 A1 | 9/2007 | Afonso |
| 2008/0188765 A1 | 8/2008 | Stolarski et al. |

FOREIGN PATENT DOCUMENTS

WO    2010054409 A1    5/2010

OTHER PUBLICATIONS

Communication of European search report issued Jul. 9, 2013; by the European Patent Office; in corresponding application No. 13157938.5.
Stiles, et al., "The Effect of Electrogram Duration on Quantification of Complex Fractionated Atrial Electrograms and Dominant Frequency", Journal of Cardiovascular Electrophysiology Duration for CFAE & DF Analysis, Mar. 3, 2008, vol. 19, No. 3, pp. 252-258.

* cited by examiner

*Primary Examiner* — Nicole F Lavert
(74) *Attorney, Agent, or Firm* — Sughrue Mion, PLLC (57) ABSTRACT

A cardiac muscle excitation waveform detector including: a waveform acquisition section that acquires, in a preset period, a waveform from an intracardiac electrocardiogram measured in middle of occurrence of atrial fibrillation; a waveform detection condition setting section that sets conditions for detecting a waveform of cardiac muscle excitation; and an excitation waveform detection section that detects a waveform of cardiac muscle excitation from the waveforms based on the conditions, wherein the waveform detection condition setting section includes a section that sets conditions based on a contour of a waveform to detect candidates for the waveform of cardiac muscle excitation, a section that sets a search period for searching for a waveform of cardiac muscle excitation; and a section that sets a preset period subsequent to detection as a detection exclusion period during which the candidate waveforms are not detected when the waveform of cardiac muscle excitation is detected.

7 Claims, 5 Drawing Sheets

CARDIAC MUSCLE EXCITATION WAVEFORM DETECTOR

BACKGROUND OF THE INVENTION

The invention relates to a cardiac muscle excitation waveform detector for detecting excitation in cardiac muscle (hereinafter simply referred to as a "cardiac muscle excitation") caused by atrial fibrillation and to a detection program.

The atrial fibrillation is high frequency tachyarrhythmia, and a mechanism of how the atrial fibrillation is maintained and medical treatment for the atrial fibrillation are under study. Medical treatment includes pharmacotherapeutics (palliative treatment), catheter ablation (curative treatment), and the like. Of these treatments, catheter ablation is for analyzing, on the basis of an intracardiac electrocardiogram, behavior of the heart experiencing atrial fibrillation; locating a region where an electric signal (an excitation waveform) called re-entry, develops, and removing the region, to thus inhibit occurrence of the re-entry.

For instance, CFE-mean (Complex Fractionated Electrogram Mean which is hereunder also called a "mean conduction time") calculation algorithm has also been proposed as a technique for analyzing an intracardiac electrocardiogram of the heart experiencing atrial fibrillation (see Non-Patent Literature 1).

[Non-Patent Literature 1] Martin K. Stiles et al., "The Effect of Electrogram Duration on Quantification of Complex Fractionated Atrial Electrograms and Dominant Frequency", Journal of Cardiovascular Electrophysiology Vol. 19, No. 3, March 2008

SUMMARY

The CFE-mean calculation algorithm is for detecting cardiac muscle excitation from an intracardiac electrocardiogram of an atrium of the heart experiencing atrial fibrillation and calculating a mean conduction time from a plurality of thus-detected patterns pertinent to the cardiac muscle excitation. First, waveform data are acquired for a predetermined period from the intracardiac electrocardiogram, and waveform contour conditions are applied to the thus-acquired waveform, thereby detecting a waveform meeting the conditions as a waveform of the cardiac muscle excitation. Next, a predetermined period subsequent to detection of the waveform of the cardiac muscle excitation is set as a detection-of-excitation-in-cardiac-muscle exclusion period. Waveforms of cardiac muscle excitation developed in the exclusion period (referred to as "Refractory" in Non-Patent Literature 1) are excluded without detection. A waveform again meeting the contour conditions after elapse of the exclusion period is detected as a waveform of cardiac muscle excitation. A mean conduction time is calculated from the thus-detected waveform of the cardiac muscle excitation.

However, under the method for calculating the mean conduction time of cardiac muscle excitation disclosed in Non-Patent Literature 1, the waveform contour is employed as conditions to be met. Therefore, for instance, when noise occurs and when a waveform of the noise meets the contour conditions, there arises a problem of the noise waveform being detected as a waveform of cardiac muscle excitation. For this reason, the following has sometimes occurred. Namely, when the noise waveform is detected as a waveform of cardiac muscle excitation, true cardiac muscle excitation that has developed in the exclusion period subsequent to detection of the noise waveform cannot be detected. Or the noise waveform is detected as a waveform of cardiac muscle excitation, and a waveform of cardiac muscle excitation is also detected. As a consequence, the noise and the cardiac muscle excitation are doubly counted. In these cases, therefore, the mean conduction time cannot be calculated correctly. This might make it impossible to precisely locate a region in the heart where re-entry occurs.

Accordingly, the invention has been conceived in light of the problems and aims at providing a cardiac muscle excitation waveform detector that is enhanced in accuracy of detection of a waveform of cardiac muscle excitation and that calculates a mean conduction time of cardiac muscle excitation more accurately, and a detection program.

It is therefore an aspect of the invention to provide a cardiac muscle excitation waveform detector comprising:

a waveform acquisition section that acquires, in a preset waveform analysis period, a waveform from an intracardiac electrocardiogram measured in middle of occurrence of atrial fibrillation;

a waveform detection condition setting section that sets conditions for detecting a waveform of cardiac muscle excitation, which shows occurrence of excitation in cardiac muscle, from among waveforms that are acquired by the waveform acquisition section in the waveform analysis period; and an excitation waveform detection section that detects a waveform of cardiac muscle excitation from the waveforms belonging to the waveform analysis period on the basis of the conditions set by the waveform detection condition setting section, wherein the waveform detection condition setting section includes a candidate waveform detection condition setting section that sets conditions based on a contour of a waveform in order to detect candidates for the waveform of cardiac muscle excitation, a search period setting section that sets a search period for searching for a waveform of cardiac muscle excitation from among the candidate waveforms detected according to the conditions based on the contour of the waveform; and a detection exclusion period setting section that sets a preset period subsequent to detection as a detection exclusion period during which the candidate waveforms are not detected as a waveform of cardiac muscle excitation when the waveform of cardiac muscle excitation is detected from the candidate waveforms.

The cardiac muscle excitation waveform detector of the first invention can diminish chances of erroneous detection and double counting of a waveform of cardiac muscle excitation and a noise waveform and enhance accuracy in detecting the waveform of cardiac muscle excitation.

The conditions for searching for the waveform of cardiac muscle excitation in the search period set by the search period setting section may be based on a maximum P-P value of the candidate waveform belonging to the search period.

The cardiac muscle excitation waveform detector of the second invention takes a waveform of the closest region as a waveform of cardiac muscle excitation and can diminish erroneous detection of the waveform of cardiac muscle excitation and the noise waveform to a much greater when compared with the first invention, so that accuracy in detecting the waveform of cardiac muscle excitation can be enhanced.

The search period setting section may set the search period so as to become shorter than the detection exclusion period.

The cardiac muscle excitation waveform detector of the third invention can diminish chances of erroneous detection of the waveform of cardiac muscle excitation and the noise waveform to a much greater extent.

The cardiac muscle excitation waveform detector may further comprise a mean conduction time calculation section that calculates a mean conduction time during which cardiac muscle excitation is conducted, from the plurality of waveforms of cardiac muscle excitation detected by the excitation waveform detection section.

In addition to yielding the same advantages as those yielded by the first through third inventions, the cardiac muscle excitation waveform detector of the fourth invention can accurately calculate a mean conduction time of cardiac muscle excitation and correctly locate a position of a region where re-entry has occurred.

It is another aspect of the invention to provide a cardiac muscle excitation waveform detection program for causing a computer to execute processing pertinent to:

a waveform acquisition procedure for measuring a size of a waveform which occurs in a preset waveform analysis period of an intracardiac electrocardiogram measured in middle of occurrence of atrial fibrillation, thereby acquiring a waveform meeting predetermined conditions as a candidate for a waveform of cardiac muscle excitation;

a cardiac muscle excitation detection procedure for taking as a cardiac muscle excitation search period a preset period that continues from occurrence of the waveform first acquired as the candidate waveform and detecting a candidate waveform which has the maximum P-P value in the cardiac muscle excitation search period as a waveform of cardiac muscle excitation; and a cardiac muscle excitation exclusion procedure for taking as a waveform detection exclusion period a preset period that continues from occurrence of the waveform detected as a candidate for a waveform of cardiac muscle excitation and detecting the candidate waveform belonging to the waveform detection exclusion period as a waveform of cardiac muscle excitation.

The cardiac muscle excitation waveform detection program of the fifth invention makes it possible to diminish chances of erroneous detection and double counting of a waveform of cardiac muscle excitation and a noise waveform and enhance accuracy in detecting the waveform of cardiac muscle excitation.

The cardiac muscle excitation waveform detection program for causing a computer to perform processing may further comprise:

processing pertinent to a procedure for iterating processing pertinent to the cardiac muscle excitation detection procedure and the cardiac muscle excitation exclusion procedure after elapse of the waveform detection exclusion period; and processing pertinent to a mean conduction time calculation procedure for calculating a mean conduction time during which cardiac muscle excitation is conducted, from a plurality of detected waveforms of cardiac muscle excitation.

In addition to yielding the same advantage as that yielded by the fifth invention, the cardiac muscle excitation waveform detection program of the sixth invention makes it possible to accurately calculate a mean conduction time of cardiac muscle excitation and correctly locate a position of a region where re-entry has occurred.

BRIEF DESCRIPTION OF THE DRAWINGS

FIGS. 2A to 2C are waveforms showing detection conditions for detecting a waveform of cardiac muscle excitation, wherein

FIGS. 5A to 5C are charts showing an embodiment, wherein

DETAILED DESCRIPTION OF EMBODIMENTS

An embodiment of a cardiac muscle excitation waveform detector of the invention is hereunder described by reference to the accompanying drawings.

Figure 1:
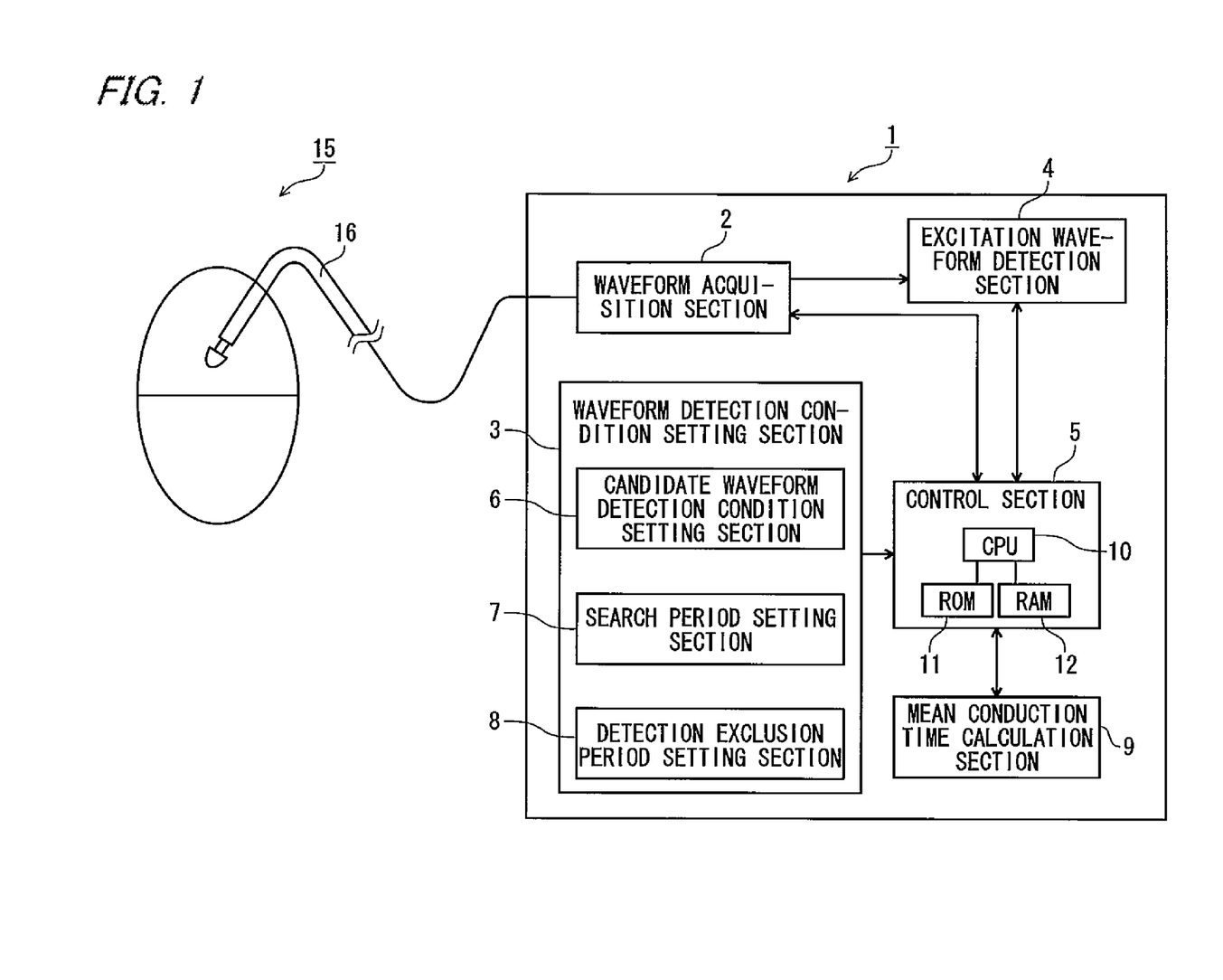
FIG. 1 is a block diagram showing a configuration of a cardiac muscle excitation waveform detector according to an embodiment of the invention.

A cardiac muscle excitation waveform detector 1 shown in FIG. 1 has a waveform acquisition section 2 that acquires a waveform meeting predetermined conditions from among measured intracardiac electrocardiogram waveforms; a waveform detection condition setting section 3 that sets terms and conditions for detecting a waveform of cardiac muscle excitation; an excitation waveform detection section 4 that detects a waveform of cardiac muscle excitation according to the conditions set by the waveform detection condition setting section 3; a mean conduction time calculation section 9 that calculates a mean conduction time during which cardiac muscle excitation is conducted; and a control section 5 that controls these sections.

The waveform detection condition setting section 3 is equipped with a candidate waveform detection condition setting section 6 that sets conditions for detecting a candidate for a waveform of cardiac muscle excitation, a search period setting section 7 that sets a search period for searching a waveform of cardiac muscle excitation from among candidate waveforms, and a detection exclusion period setting section 8 that sets a detection exclusion period not for detecting the candidate waveform as the waveform of cardiac muscle excitation.

Further, reference numeral 15 shown in FIG. 1 schematically shows the heart whose intra-atrial intracardiac electrocardiogram is under measurement. A cardiac catheter 16 is inserted in an atrium from a peripheral blood vessel, and an intracardiac electrocardiogram is acquired by way of electrodes (not shown) attached to the cardiac catheter 16. The thus-acquired intracardiac electrocardiogram waveform are sent to the cardiac muscle excitation waveform detector 1 by way of the cardiac catheter 16 and acquired by the waveform acquisition section 2 of the cardiac muscle excitation waveform detector 1.

The waveform acquisition section 2 acquires intracardiac electrocardiogram waveform data on the basis of a waveform acquisition control signal sent from the control section 5. The waveform acquisition control signal includes control signals, like timing and an acquisition period for acquiring intracardiac electrocardiogram waveform data. A waveform analysis period according to the embodiment of the invention is an example of a period for acquiring intracardiac electrocardiogram waveform data, and a preset waveform analysis period is sent from the control section 5 to the waveform acquisition section 2 as a control signal pertinent to an acquisition period. The waveform acquisition section 2 received the control signal acquires from acquisition timing intracardiac electrocardiogram waveform data belonging to the waveform analysis period. The thus-acquired intracardiac electrocardiogram waveform data are sent to the excitation waveform detection section 4 and stored and retained in RAM 12 provided in the control section 5.

The waveform detection condition setting section 3 sets conditions for detecting, from a waveform that has been acquired by the waveform acquisition section 2 and that belongs to an intracardiac electrocardiogram waveform data acquisition period (e.g., the waveform analysis period), a waveform of cardiac muscle excitation which shows occurrence of excitation in cardiac muscle (i.e., an electrical signal of an excitation waveform).

Figure 2A:
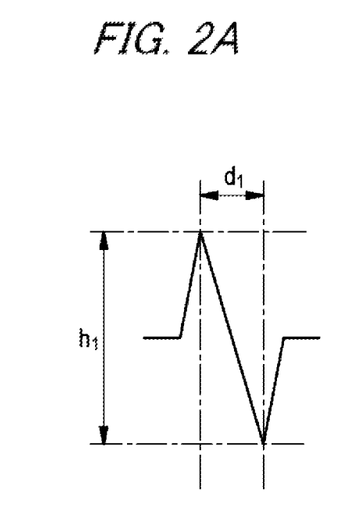
FIG. 2A shows contour conditions for a waveform to be detected.

In order to detect a candidate for the waveform of excitation in cardiac muscle, the candidate waveform detection condition setting section 6 provided in the waveform detection condition setting section 3 sets detection conditions on the basis of the data pertinent to a contour of a waveform. For instance, data pertinent to a horizontal width and a vertical width of an electric potential indicated by the intracardiac electrocardiogram waveform belonging to the waveform analysis period are set as analysis conditions. A waveform shown in FIG. 2A represents an example of acquired intracardiac electrocardiogram waveform data. A horizontal width and a vertical width of a waveform (an electric potential) set as detection conditions are set as an arrowheaded width d1 and an arrowheaded height h1, respectively. Specifically, the detection conditions for detecting a candidate for the waveform of cardiac muscle excitation are set to; for instance, the horizontal width d1 of an intracardiac electrocardiogram waveform being 10 msec or less and the vertical width h1 being 0.1 mV or more. The data pertinent to the waveform contour that serves as the conditions for detecting a set candidate waveform are sent to the control section 5 and stored and retained in the RAM 12 provided in the control section 5.

Data pertinent to the waveform contour that serves as conditions for detecting a candidate waveform are sent from the control section 5 to the excitation waveform detection section 4. The excitation waveform detection section 4 detects, from the intracardiac electrocardiogram waveform data acquired by the waveform acquisition section 2, a waveform meeting the candidate waveform detection conditions and determines the thus-detected waveform as a candidate waveform of cardiac muscle excitation.

The search period setting section 7 provided in the waveform detection condition setting section 3 sets a search period for searching for a waveform of cardiac muscle excitation from an intracardiac electrocardiogram waveform that meets the detection conditions based on the data pertinent to the waveform contour set by the candidate waveform detection condition setting section 6 and that is detected by the excitation waveform detection section 4 as a candidate waveform for cardiac muscle excitation. The search period is a period that is set in order to inhibit erroneous detection of a noise waveform as a waveform of cardiac muscle excitation. The search period is set to a period that is shorter than the detection exclusion period (which will be descried later). Data pertinent to the thus-set search period are sent to the control section 5 and stored and retained in the RAM 12 provided in the control section 5.

Also, data pertinent to the search period are sent from the control section 5 to the excitation waveform detection section 4. The excitation waveform detection section 4 measures a maximum P-P value (a value from the highest positive value to the highest negative value of the waveform) of the candidate waveform of cardiac muscle excitation belonging to the search period. Data based on the thus-measured maximum P-P value are set as conditions for searching for a waveform of cardiac muscle excitation. Specifically, there are set, as conditions, searching for a candidate waveform of cardiac muscle excitation with the maximum P-P value from candidate waveforms of cardiac muscle excitation belonging to the search period. The excitation waveform detection section 4 determines as a waveform of cardiac muscle excitation a candidate waveform with the maximum P-P value that is detected by the search. As a result of the search period being set as mentioned above, when a plurality of candidate waveforms are present in the search period, only the candidate waveform with the maximum P-P value can be determined as a waveform of cardiac muscle excitation. Accordingly, it is possible to inhibit a noise waveform from being erroneously detected as a waveform of cardiac muscle excitation.

Figure 2B:
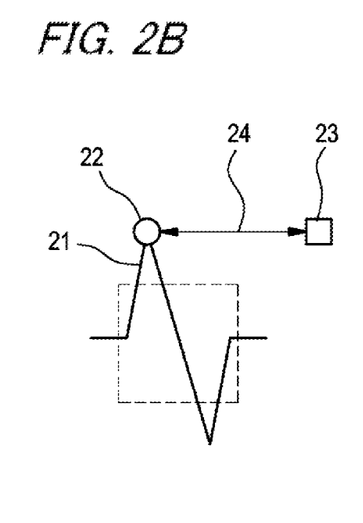
FIG. 2B shows conditions for a waveform search period.

Data pertinent to the thus-determined waveform of cardiac muscle excitation are sent to the control section 5 and stored and retained in the RAM 12 provided in the control section 5. FIG. 2B is a drawing schematically showing a set search period. A period, depicted by an arrow 24, from a peak (depicted by an outlined circle) 22 to an outlined square 23 of a candidate waveform 21 of cardiac muscle excitation that was first detected by the excitation waveform detection section 4 is set as a search period. The candidate waveform that belongs the search period and that exhibits the maximum P-P value is defined as a waveform of cardiac muscle excitation. In the search period shown in FIG. 2B, only one candidate waveform 21 is present in the search period 24, and hence the candidate waveform 21 is determined as a waveform of cardiac muscle excitation.

When the waveform of cardiac muscle excitation is detected from the candidate waveform detected by the excitation waveform detection section 4, the detection exclusion period setting section 8 provided in the waveform detection condition setting section 3 sets a preset period subsequent to detection as a detection exclusion period during which cardiac muscle excitation is not detected. The detection exclusion period is a period provided in order to inhibit a candidate waveform including a noise waveform from being doubly counted. The detection exclusion period can be set to; for instance, 50 msec by physiologically determining a cycle of local activation in the heart.

Figure 2C:
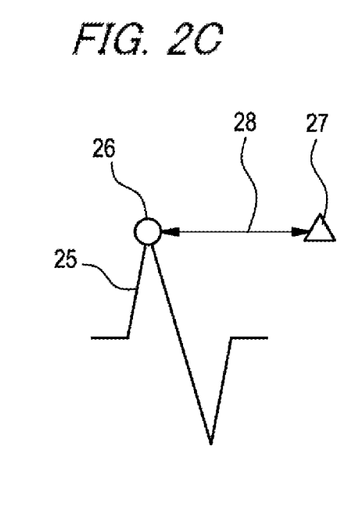
FIG. 2C shows conditions for a waveform detection exclusion period.

Data pertinent to the set detection exclusion period are sent to the control section 5 and stored and retained in the RAM 12 provided in the control section 5. FIG. 2C is a drawing which schematically shows the set detection exclusion period. A period, depicted by an arrow 28, from a peak (depicted by an outlined circle) 26 to an outlined triangle 27 of a waveform 25 of cardiac muscle excitation that was determined by the excitation waveform detection section 4 is set as a detection exclusion period. Candidate waveforms of cardiac muscle excitation that are present in the period are excluded from a target of analysis. In the case shown in FIG. 2C, only the waveform 25 of cardiac muscle excitation is present in the detection exclusion period 28, and other candidate waveforms are not present, and, hence, a target waveform to be excluded from analysis is not present either.

Details of the conditions set by the waveform detection condition setting section 3 (including the candidate waveform detection condition setting section 6, the search period setting section 7, and the detection exclusion period setting section 8) can be set and changed from the outside. Setting condition input means (omitted from the drawings) which is connected to and provided in the waveform detection condition setting section 3 may also be enabled to input and change the details.

In accordance with the detection control signal sent from the control section 5, the excitation waveform detection section 4 detects the candidate waveform fulfilling the conditions set by the waveform detection condition setting section 3 (the candidate waveform detection condition setting section 6, the search period setting section 7, and the detection exclusion period setting section 8) as a waveform of cardiac muscle excitation. The excitation waveform detection section 4 also has, such as those mentioned above, a function of determining a candidate waveform of cardiac muscle excitation on the basis of the set conditions and a function of defining a waveform of cardiac muscle excitation on the basis of the same. Data detected and defined by the excitation waveform detection section 4 are sent to the control section 5 and stored and retained in the RAM 12 provided in the control section 5.

In accordance with a calculation control signal sent from the control section 5, the mean conduction time calculation section 9 calculates a mean conduction time during which cardiac muscle excitation is conducted, from the data pertinent to the plurality of waveforms of cardiac muscle excitation detected by the excitation waveform detection section 4. The time during which cardiac muscle excitation is conducted refers to a time interval between detected waveforms of cardiac muscle excitation. An average of the time intervals is taken as a mean conduction time. Data pertinent to a mean conduction time calculated by the mean conduction time calculation section 9 are transmitted to the control section 5 and stored and retained in the RAM 12 provided in the control section 5.

The control section 5 controls the individual sections (the waveform acquisition section 2, the excitation waveform detection section 4, and the mean conduction time calculation section 9) of the cardiac muscle excitation waveform detector 1 on the basis of the conditions set by the waveform detection condition setting section 3 (the candidate waveform detection condition setting section 6, the search period setting section 7, and the detection exclusion period setting section 8). The control section 5 is equipped with a CPU 10 that supervises control; ROM 11, as a computer readable media, that retains programs for executing processing of various processing procedures pertinent to the CPU; and the RAM 12 that stores various data for the respective sections (the acquisition section, the setting sections, the detection section, and the calculation section, and others) that serve as a work area of the CPU.

By adoption of the configuration, such as that mentioned above, erroneous detection of a noise waveform can be inhibited, so that accuracy in detecting a waveform of cardiac muscle excitation can be enhanced. Accordingly, an accurate conduction time of cardiac muscle excitation can be measured, and a more correct mean conduction time can be calculated. Further, the functions of the cardiac muscle excitation waveform detector are also effective in analyzing a waveform of cardiac muscle excitation in real time and analyzing the waveform of cardiac muscle excitation for reviewing and commenting purposes and the like.

Figure 3:
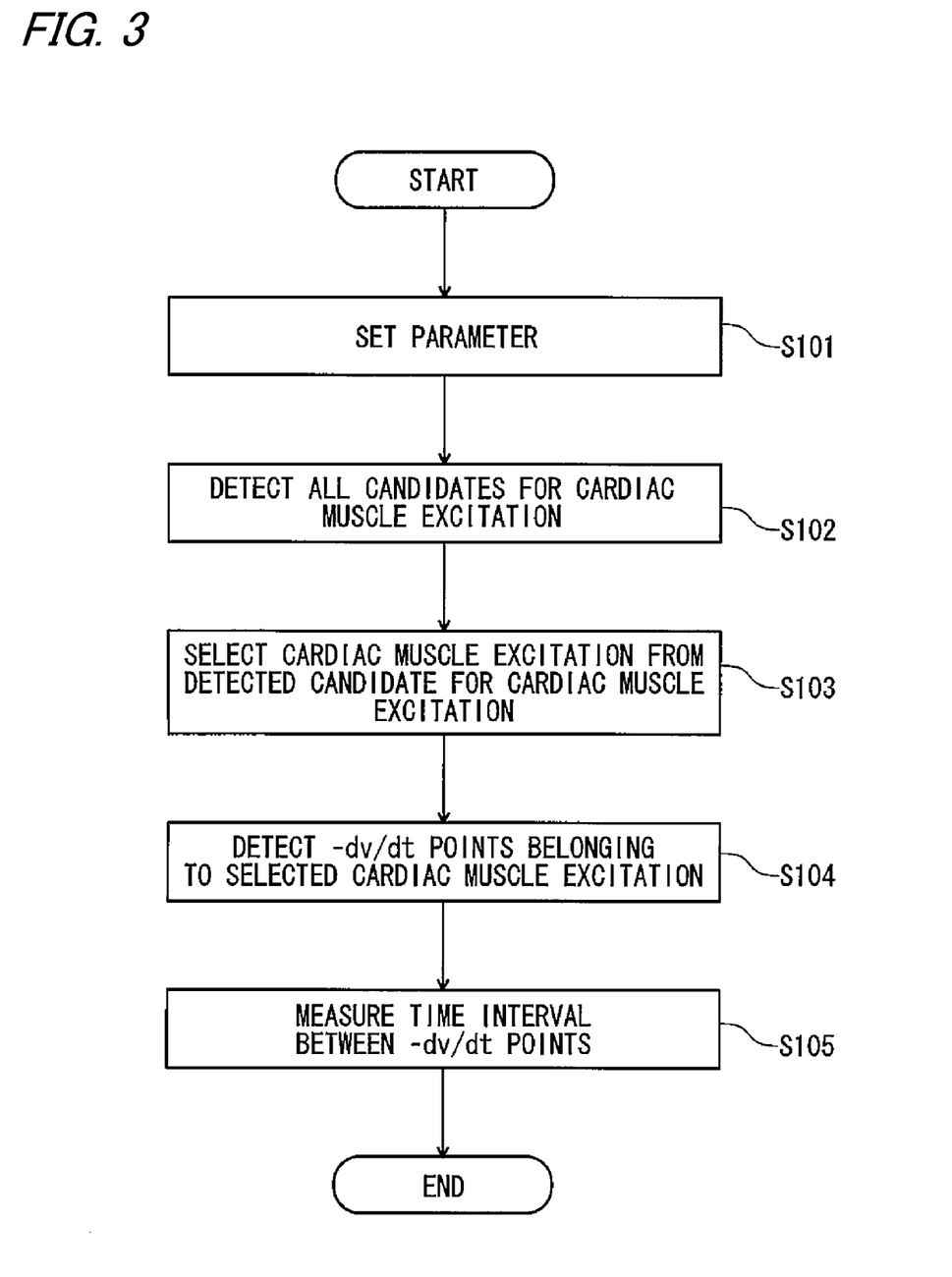
FIG. 3 is a flowchart showing procedures of processing for detecting a waveform of cardiac muscle excitation.

Processing procedures of cardiac muscle excitation waveform detection processing are now described along a flowchart shown in FIG. 3. Incidentally, on the occasion of explanation of the processing procedures, explanations are provided by reference to FIG. 4 that shows procedures for detecting a waveform of cardiac muscle excitation.

When processing for detecting a waveform of cardiac muscle excitation is commenced, settings of parameters for detecting a waveform of cardiac muscle excitation are first made (step S101). For instance, there are set parameters based on contour data on a waveform that are set by the candidate waveform detection condition setting section 6 in order to detect a candidate for a waveform of cardiac muscle excitation. Specifically, a horizontal width and a vertical width of an intracardiac electrocardiogram waveform (an electric potential) acquired by the waveform acquisition section 2 are set to a value of 10 msec or less and a value of 0.1 mV or more, respectively. Next, there are set parameters pertinent to a detection exclusion period (an analysis target exclusion period) that is set by the detection exclusion period setting section 8 and during which none of the candidate waveforms are detected as a waveform of cardiac muscle excitation. Specifically, the detection exclusion period is set to 50 msec. Subsequently, there are set parameters pertinent to a search period that is set by the search period setting section 7 in order to search for a waveform of cardiac muscle excitation. Specifically, a search period is set to 49 msec. The search period is at this time set to a period of time that is shorter than the detection exclusion period.

Figure 4:
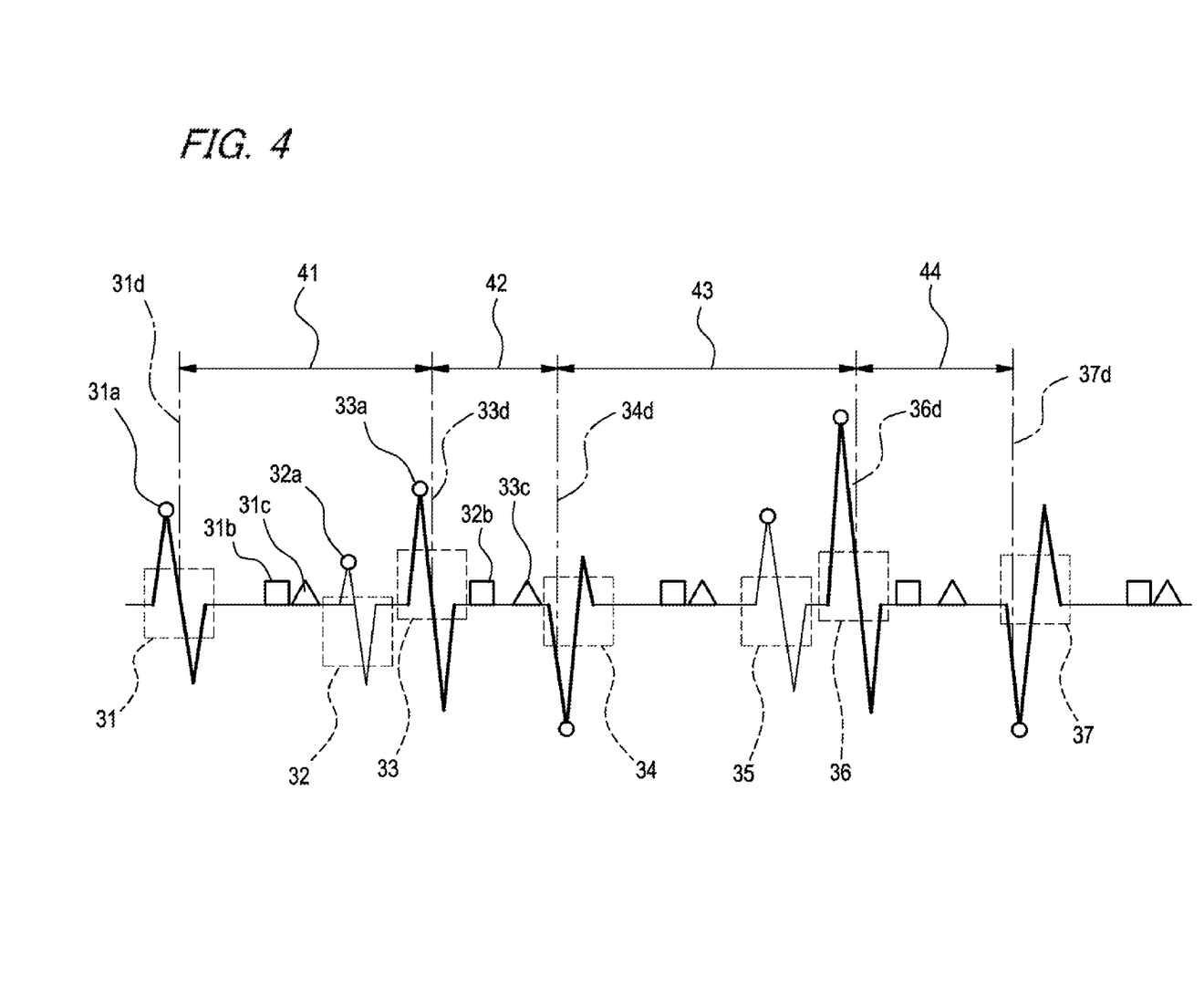
FIG. 4 is a chart showing procedures for detecting a waveform of cardiac muscle excitation from a waveform of an obtained intracardiac electrocardiogram.

The waveform shown in FIG. 4 is a part of a waveform that the waveform acquisition section 2 acquired, in the waveform analysis period, from the intracardiac electrocardiogram waveform measured in the middle of occurrence of atrial fibrillation. The waveform analysis period is a preset period (set to 5 sec in the embodiment) and is sent as an analysis control signal from the control section 5 to the waveform acquisition section 2. In accordance with the analysis control signal, the waveform acquisition section 2 acquires a waveform during a period of five seconds.

Subsequently, all waveforms meeting the conditions set in S101; namely, the horizontal width (10 msec or less) and the vertical width (0.1 mV or more), are detected as candidates for a waveform of cardiac muscle excitation from the intracardiac electrocardiogram waveform that occurred in the waveform analysis period and was acquired by the waveform acquisition section 2 (step S102). Step S102 is an example of waveform acquisition procedures of the invention. In FIG. 4, seven waveforms belonging to squares 31 to 37 designated by broken lines are detected as candidates for a waveform of cardiac muscle excitation.

Subsequently, a waveform of cardiac muscle excitation is selected from among the candidates for a waveform of cardiac muscle excitation detected in step S102 (step S103). In FIG. 4, the excitation waveform detection section 4 measures a P-P value of the first detected candidate waveform (i.e., a waveform belonging to the square 31 designated by broken lines). Next, a search is made as to whether or not another candidate waveform (another waveform belonging to the square designated by broken lines) is in a period that ranges from a point designated by an outlined circle 31*a* to a point designated by an outlined square 31*b* until which the search period (49 msec) elapsed from the point 31*a*. In FIG. 4, there is not any other candidate waveform except the waveform belonging to the square 31 designated by broken lines. Hence, the waveform belonging to the square 31 designated by broken lines is defined as a first waveform of cardiac muscle excitation. A period ranging from the first peak (designated by the solid circle 31*a*) of the thus-defined waveform of cardiac muscle excitation to a point designated by a solid triangle 31*c* until which a detection exclusion period (50 msec) elapsed from the first peak 31*a* is taken as an analysis target exclusion period during which no waveforms are detected.

After elapse of the analysis target exclusion period (subsequent to the solid triangle 31*c*), the excitation waveform detection section 4 measures a P-P value of a candidate waveform (a waveform belonging to the square 32 designated by broken lines) first detected. Next, a search is made as to whether or not another candidate waveform (another waveform belonging to the square designated by broken lines) is in a period that ranges from a point designated by a solid circle 32a to a point designated by a solid square 32b until which the search period (49 msec) elapsed from the point 32a. When there is another candidate waveform, a P-P value of the candidate waveform is measured and compared with the P-P value of the waveform included in the square 32 designated by broken lines. In FIG. 4, since another candidate waveform (a waveform belonging to the square 33 designated by broken lines) belongs to a period which ranges from the solid circle 32a to the solid square 32b, a P-P value of the candidate waveform is measured and compared with the P-P value of the waveform belonging to the square 32 designated by broken lines. When a plurality of candidate waveforms are present in the search period, a candidate waveform having the largest P-P value is detected and defined as a waveform of cardiac muscle excitation. When the P-P value of the waveform belonging to the square 32 designated by broken lines is compared with the P-P value of the waveform belonging to the square 33 designated by broken lines, the P-P value of the waveform belonging to the square 33 designated by broken lines is, as is obvious from FIG. 4, larger than the P-P value of the waveform belonging to the square 32 designated by broken lines. Accordingly, the candidate waveform belonging to the square 33 designated by broken lines is defined as a waveform of cardiac muscle excitation. The reason why the waveform having the largest P-P value is defined as a waveform of cardiac muscle excitation by comparison of the plurality of candidate waveforms is for taking, as a waveform of cardiac muscle excitation, an intracardiac electrocardiogram waveform appeared at a region closest to an electrode (not shown) that acquires the intracardiac electrocardiogram waveform. The waveform that is not defined as a waveform of cardiac muscle excitation and belongs to the square 32 designated by broken lines is not hereafter used as a waveform for the purpose of calculating a mean conduction time during which cardiac muscle excitation is conducted. A period ranging from the first peak (designated by a solid circle 33a) of the thus-defined waveform of cardiac muscle excitation to a point designated by a solid triangle 33c until which a detection exclusion period (50 msec) elapsed from the first peak 33a is taken as an analysis target exclusion period during which no waveforms are detected. Foregoing detection processing is iterated until the waveform analysis period ends, thereby repeatedly detecting a waveform of cardiac muscle excitation.

Next, −dv/dt point in the selected waveform of cardiac muscle excitation is detected after completion of detection of the waveform of cardiac muscle excitation (step S104). In FIG. 4, points 31d, 33d, 34d, 36d, and 37d all of which are designated by broken lines are detected. Points detected from the waveform are not limited to the −dv/dt point, and a dv/dt point can also be detected.

Subsequently, a duration between the −dv/dt points detected in step S104; namely, a conduction time during which cardiac muscle excitation was conducted, is measured, and a mean conduction time is calculated from the thus-measured respective conduction times (step S105). In FIG. 4, a duration between the points 31d and 33d, a duration between the points 33d and 34d, a duration between the points 34d and 36d, and a duration between the points 36d and 37d are respectively measured as conduction times 41, 42, 43, and 44 during which cardiac muscle excitation is conducted. A mean conduction time is calculated from the conduction times.

Figure 5A:
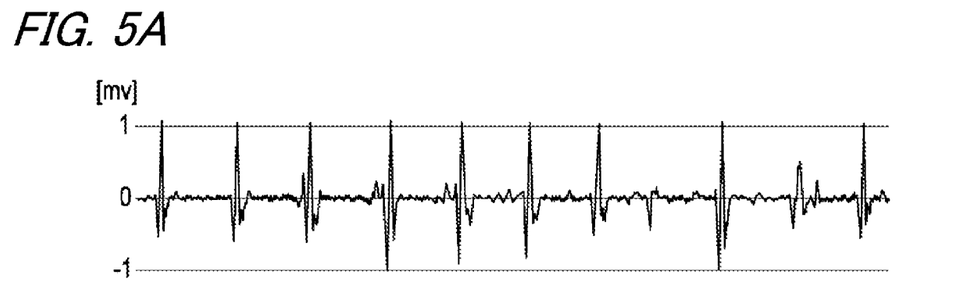
FIG. 5A shows an intracardiac electrocardiogram waveform of the heart experiencing atrial fibrillation.

Explanations are now given to a result of calculation of a mean conduction time (see FIG. 5B) by subjecting the intracardiac electrocardiogram waveform (see FIG. 5A) appeared in the middle of occurrence of atrial fibrillation to the related art analysis technique (the technique described in connection with Non-Patent Literature 1) and a result of calculation of a mean conduction time (see FIG. 5C) by subjecting the intracardiac electrocardiogram waveform (see FIG. 5A) appeared in the middle of occurrence of atrial fibrillation to the analysis technique of the invention.

The parameters pertinent to the conditions for detecting a waveform are set to a horizontal width of 10 msec or less, a vertical width of 0.1 mV or more, a detection exclusion period of 50 msec, and a search period of 49 msec.

Figure 5B:
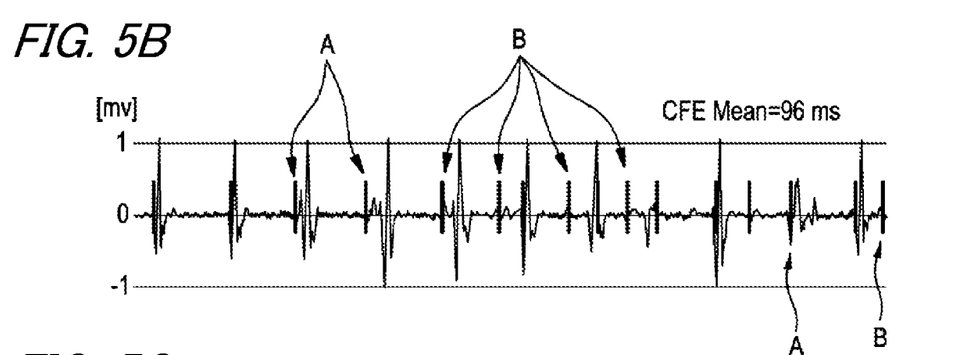
FIG. 5B shows a result of a mean conduction time being calculated under a related-art analysis technique.

Symbols A and B in FIG. 5B designate regions where the noise waveform was detected as a waveform of cardiac muscle excitation as a result of having fulfilled the contour waveform conditions. It can be ascertained that a waveform of true cardiac muscle excitation followed the noise waveform designated by symbol A but was not detected under influence of the detection exclusion period. Moreover, it can also be ascertained that the waveform of true cardiac muscle excitation following the noise waveform designated by symbol B was detected and that both the noise waveform and the true excitation waveform were detected (a so-called double count).

As above, the waveform of cardiac muscle excitation was detected by means of the related art analysis technique, and the mean conduction time was calculated from the thus-detected waveform of cardiac muscle excitation. The mean conduction time was 96 msec. In the regions where both the noise waveform and the waveform of true cardiac muscle excitation were detected, a duration between the waveforms is short, and the conduction time is also short. For these reasons, it can be inferred that a mean conduction time becomes smaller than a true value under the influence of the noise waveform. It can also be inferred that the noise waveform also affects the accuracy of the calculated mean conduction time even in the regions where the noise waveform is detected in place of the waveform of true cardiac muscle excitation.

Figure 5C:
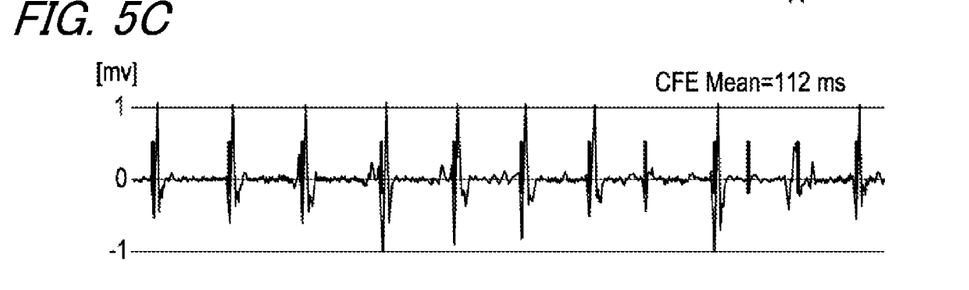
FIG. 5C shows a result of a mean conduction time being calculated under an analysis technique of the invention.

In the meantime, when the analysis technique of the invention was conducted, the occurrence of erroneous detection of the noise waveform is significantly diminished as shown in FIG. 5C, and almost all detected waveforms represent waveforms of true cardiac muscle excitation. As a result of the mean conduction time being calculated from the thus-detected waveforms of cardiac muscle excitation, it can be confirmed that the mean conduction time is 112 msec and that influence of the noise waveform is eliminated. In other words, it can be confirmed that the mean conduction time can be calculated more accurately than that is calculated by the related art analysis technique.

The processing procedures described in connection with the embodiment of the invention can also be embodied as a method including a series of procedures. Alternatively, the series of procedures can also be materialized as an invention of a program that causes a computer to execute processing pertinent to the series of procedures. In this case, the program is recorded in a computer readable media. As a computer readable media, ROM can be used as described above. In addition, any kinds of well known computer readable media can be utilized to record the program. Even in these cases, advantages similar to that mentioned in connection with the embodiment can also be yielded.

The invention makes it possible to inhibit occurrence of erroneous detection and double counting of a waveform of cardiac muscle excitation and a noise waveform and enhance accuracy in detecting the waveform of cardiac muscle excitation. Moreover, the invention also makes it possible to accurately calculate a mean conduction time of cardiac muscle excitation and correctly locate a position of a region where re-entry has occurred.

What is claimed is:

1. A cardiac muscle excitation waveform detector comprising:
   a waveform acquisition section configured to acquire, in a preset waveform analysis period, a waveform from an intracardiac electrocardiogram measured in middle of occurrence of atrial fibrillation;
   a waveform detection condition setting section configured to set conditions for detecting a waveform of cardiac muscle excitation, which shows occurrence of excitation in cardiac muscle, from among waveforms that are acquired by the waveform acquisition section in the waveform analysis period; and
   an excitation waveform detection section configured to detect a waveform of cardiac muscle excitation from the waveforms belonging to the waveform analysis period on the basis of the conditions set by the waveform detection condition setting section, wherein
   the waveform detection condition setting section includes
   a candidate waveform detection condition setting section configured to set conditions based on a contour of a waveform in order to detect candidates for the waveform of cardiac muscle excitation,
   a search period setting section configured to set a search period for searching for a waveform of cardiac muscle excitation from among the candidate waveforms detected according to the conditions based on the contour of the waveform; and
   a detection exclusion period setting section configured to set a preset period subsequent to detection as a detection exclusion period during which the candidate waveforms are not detected as a waveform of cardiac muscle excitation when the waveform of cardiac muscle excitation is detected from the candidate waveforms.

2. The cardiac muscle excitation waveform detector according to claim 1, wherein the conditions for searching for the waveform of cardiac muscle excitation in the search period set by the search period setting section are based on a maximum P-P value of the candidate waveform belonging to the search period.

3. The cardiac muscle excitation waveform detector according to claim 1, wherein the search period setting section sets the search period so as to become shorter than the detection exclusion period.

4. The cardiac muscle excitation waveform detector according to claim 1, further comprising a mean conduction time calculation section configured to calculate a mean conduction time during which cardiac muscle excitation is conducted, from the plurality of waveforms of cardiac muscle excitation detected by the excitation waveform detection section.

5. The cardiac muscle excitation waveform detector according to claim 1, wherein the excitation waveform detection section determines one of the candidate waveforms having the largest P-P value of the candidate waveforms as the waveform of the cardiac muscle excitation.

6. A non-transitory computer-readable medium having embodied thereon a cardiac muscle excitation waveform detection program for causing a computer to execute processing pertinent to:
   a waveform acquisition procedure for measuring a size of a waveform which occurs in a preset waveform analysis period of an intracardiac electrocardiogram measured in middle of occurrence of atrial fibrillation, thereby acquiring a waveform meeting predetermined conditions as a candidate for a waveform of cardiac muscle excitation;
   a cardiac muscle excitation detection procedure for taking as a cardiac muscle excitation search period a preset period that continues from occurrence of the waveform first acquired as the candidate waveform and detecting a candidate waveform which has the maximum P-P value in the cardiac muscle excitation search period as a waveform of cardiac muscle excitation; and
   a cardiac muscle excitation exclusion procedure for taking as a waveform detection exclusion period a preset period that continues from occurrence of the waveform detected as a candidate for a waveform of cardiac muscle excitation and detecting the candidate waveform belonging to the waveform detection exclusion period as a waveform of cardiac muscle excitation.

7. The non-transitory computer-readable medium according to claim 6, wherein the cardiac muscle excitation waveform detection program further causes the computer to execute processing pertinent to:
   a procedure for iterating processing pertinent to the cardiac muscle excitation detection procedure and the cardiac muscle excitation exclusion procedure after elapse of the waveform detection exclusion period; and
   a mean conduction time calculation procedure for calculating a mean conduction time during which cardiac muscle excitation is conducted, from a plurality of detected waveforms of cardiac muscle excitation.

* * * * *